United States Patent
Fry et al.

(10) Patent No.: US 7,769,597 B2
(45) Date of Patent: Aug. 3, 2010

(54) SYSTEM AND METHOD FOR AUTOMATICALLY VERIFYING MULTIPLE LABORATORY TEST RESULTS IN A COMPUTERIZED ENVIRONMENT

(75) Inventors: Jeffrey D. Fry, Lansing, KS (US); Lori N. Cross, Kansas City, MO (US); Arthur J. Hauck, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1591 days.

(21) Appl. No.: 11/021,878

(22) Filed: Dec. 22, 2004

(65) Prior Publication Data

US 2006/0136263 A1    Jun. 22, 2006

(51) Int. Cl.
*G06Q 50/00*  (2006.01)
(52) U.S. Cl. .......................................... 705/2; 600/300
(58) Field of Classification Search ................. 705/2–3; 600/300
See application file for complete search history.

(56) References Cited

U.S. PATENT DOCUMENTS

| 6,018,713 | A | * | 1/2000 | Coli et al. | 705/2 |
| 6,581,012 | B1 | * | 6/2003 | Aryev et al. | 702/22 |
| 2002/0161606 | A1 | * | 10/2002 | Bennett et al. | 705/2 |

* cited by examiner

*Primary Examiner*—Gerald J. O'Connor
*Assistant Examiner*—Sind Phongsvirajati
(74) *Attorney, Agent, or Firm*—Shook, Hardy & Bacon L.L.P.

(57) ABSTRACT

The present invention relates to a method of holding laboratory test results in a computerized environment. The method receives a laboratory test result for a healthcare order for a patient. The healthcare order comprises multiple laboratory tests. The method determines whether all of the test results for the healthcare order have been received. If all of the test results for the healthcare order have not been received, the laboratory test result is held until all of the results for the healthcare order have been received. If all of the results for the healthcare order have been received, the method compares each test result of the healthcare order to predefined criteria to determine whether each test result for the healthcare order is within a predetermined acceptable range. If each of the test results for the healthcare order is within the acceptable range, the entire order is automatically verified.

8 Claims, 3 Drawing Sheets

US 7,769,597 B2

SYSTEM AND METHOD FOR AUTOMATICALLY VERIFYING MULTIPLE LABORATORY TEST RESULTS IN A COMPUTERIZED ENVIRONMENT

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates generally to the field of computer software. More particularly, the present invention relates to automatically verifying multiple laboratory tests results in a computerized environment.

BACKGROUND OF THE INVENTION

Laboratory tests are ordered for a number of reasons. For example, healthcare providers order laboratory tests to be performed for a patient in a healthcare environment. Examples of these tests include analyzing fluid or bodily tissue, such as blood or urine. A fluid or tissue sample is taken from a patient and sent to a laboratory to be tested. One or more instruments within the laboratory perform ordered tests on the sample. The instrument performs the test and provides an electronic message of the test results.

The test results are verified using a decision process to determine what is normal or otherwise acceptable for a test result for a patient. For example, verification may determine whether the test result is within a predetermined range that is considered to be acceptable for that type of laboratory test. Previously, a technologist or clinician in the laboratory verified laboratory test results. This process was time consuming and prone to human error.

Other systems have attempted to automate the decision process and verify laboratory test results electronically. The systems evaluate each result individually against predefined decision rules to determine if the result should be released by the system for clinical use. However, these systems are unable to evaluate multiple test results from the same order that are routed to different instruments, testing stations or modular instruments. The laboratory test result messages coming from different instruments may be related to one order. These systems cannot determine if the entire set of laboratory test results satisfies the predefined verification rules prior to releasing the test results. Thus, since laboratory test results can only be evaluated within the context of an individual laboratory test result, some results may be automatically verified even though subsequent related laboratory test results have information that would cause all the results in the set or order to fail automatic verification. Furthermore, these systems cannot automatically verify multiple test results received from multiple areas of modular laboratory instruments.

It would be beneficial to be able to hold laboratory test results from a set or group until all of the laboratory test results for the set or group have been received so that the results as a group may be compared to the predefined auto-verification rules and auto-verified.

SUMMARY OF THE INVENTION

In one embodiment, a method of holding laboratory test results in a computerized environment is provided. The method receives a first laboratory test result for a healthcare order for a patient. The healthcare order comprises multiple laboratory tests. The method determines whether all of the test results for the healthcare order have been received. And if all of the test results for the healthcare order have not been received, the first laboratory test result is held until all of the results for the healthcare order have been received. If all of the results for the healthcare order have been received, the method compares each test result of the healthcare order to predefined criteria to determine whether each test result for the healthcare order is within a predetermined acceptable range. If each of the test results for the healthcare order is within the acceptable range, the entire order is automatically verified.

In another embodiment, a method of receiving data from a modular laboratory instrument that performs multiple laboratory tests is described. The method receives data from a modular laboratory instrument. The data comprises laboratory test results for multiple lab tests for an order. The data from the modular laboratory instrument is parsed into individual test results for the order. Each of the individual test results in the healthcare order is compared to predefined criteria to determine whether each of the individual test results is within an acceptable range.

In yet another embodiment, a system for suspending processing of laboratory test results in a computerized environment is provided. The system includes a receiving component for receiving a first laboratory test result for a patient, where the healthcare order comprises multiple tests. The system further includes a determining component determining whether all of the test results for the healthcare order have been received and a suspending component for suspending processing of the first laboratory test result if all of the test results for the order have not been received.

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

The present invention allows the coordination of laboratory test results from multiple sources and/or interface instruments at one time. It decreases the multitude of individual orders that automatically fail general auto-verification. The present invention provides the ability to automatically verify (auto-verify) results requiring multiple instruments to perform tests for the same order and allows for auto-verification of results received from multiple areas of modular instruments.

Figure 1:
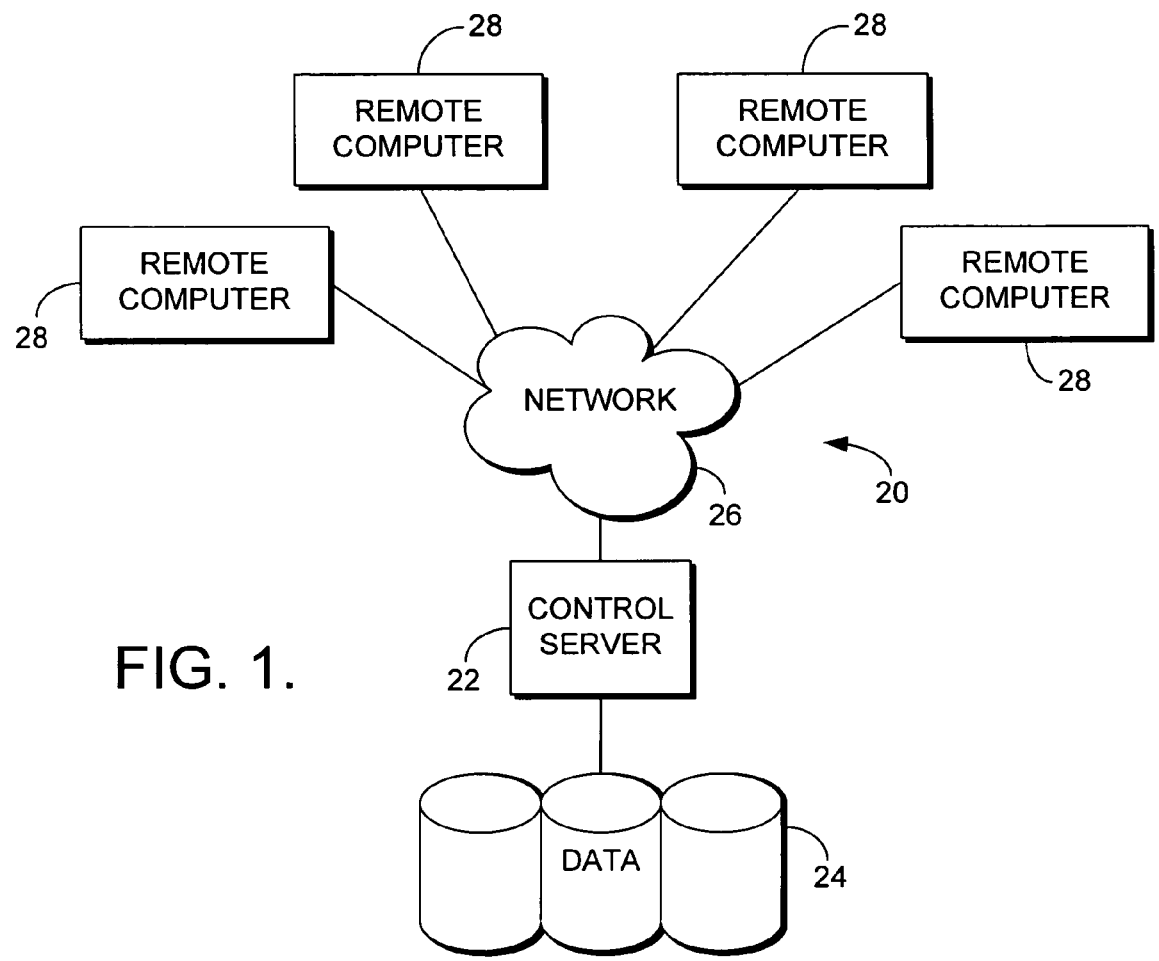
FIG. 1 is a block diagram of a computing system environment suitable for use in implementing the present invention.

With reference to FIG. 1, an exemplary medical information system for implementing the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, physician's assistants, nurse practitioners, nurses, nurse's aides, pharmacists, dieticians, microbiologists, laboratory experts, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system operating in conjunction with an Internet-based system, one skilled in the art would recognize that the method and system can be implemented in any system supporting the receipt and processing of laboratory test results.

Figure 2:
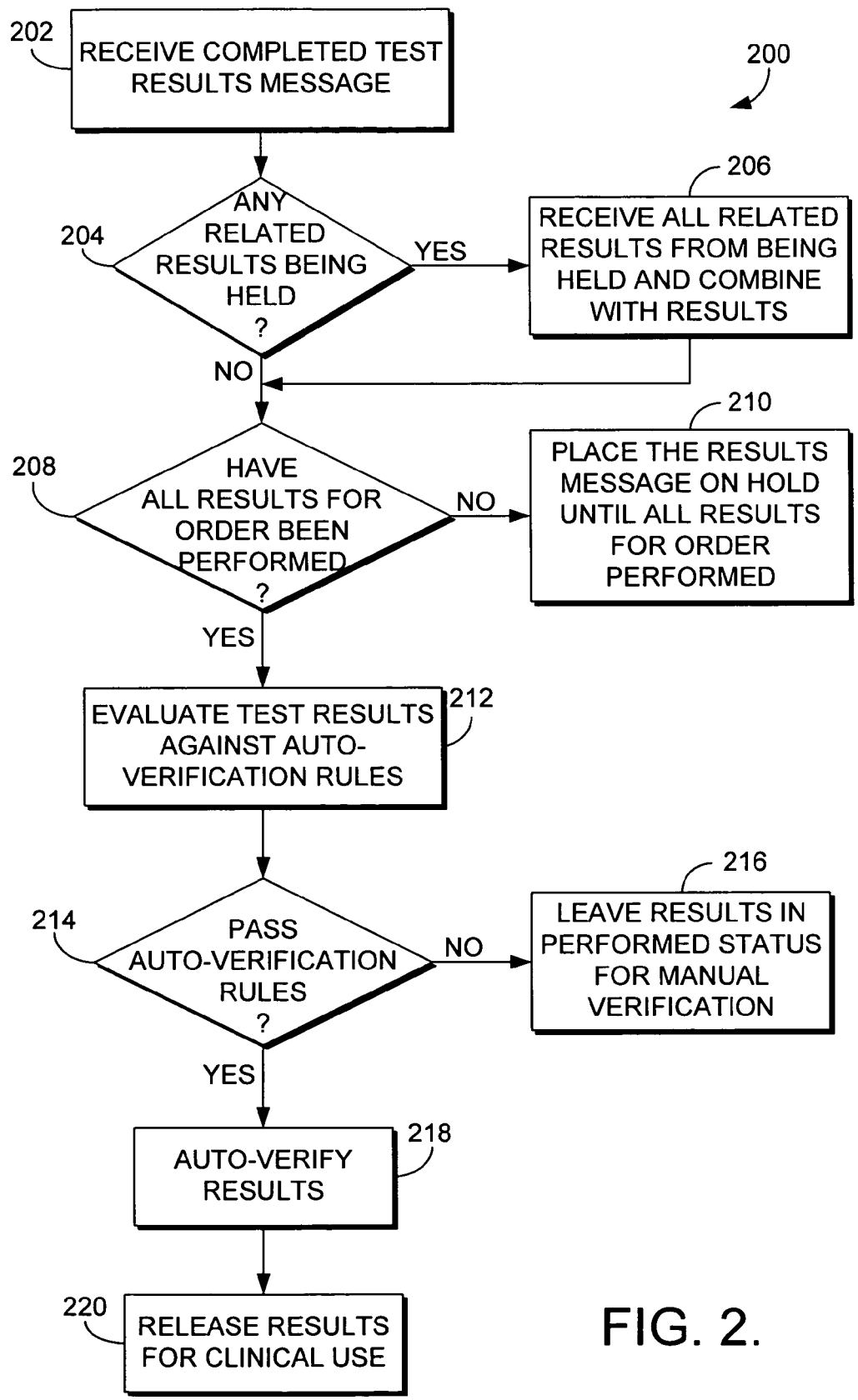
FIG. 2 is a flow chart representative of a computer program for automatically verifying a set of laboratory test results in accordance with an embodiment of the present invention.

With reference to FIG. 2, a flow chart representative of a method for automatically verifying multiple laboratory test results in accordance with an embodiment of the present invention is illustrated and depicted generally as reference numeral 200. At block 202, one or more completed test results from an instrument, result source or testing station in the laboratory are received. In one embodiment, one or more completed laboratory test results are received in the form of an electronic message. At decision block 204 it is determined whether there are any other related results to the laboratory test results received at block 202 being held. For example, it is determined whether any of the laboratory test results from the same order as the result received are being held. A healthcare order may comprise a set of related healthcare tests. For example, an order for a lipid profile comprises a cholesterol test, a triglyceride test and an HDL test. The related tests may be performed on the same or different instruments. Thus, if a result for an HDL test for the patient is received, at block 202, the system determines if the results for the cholesterol and triglyceride tests have been received.

If, at block 204, it is determined there are related results, being held at block 206, laboratory results related to the results received at block 202 are received. The related results are combined with the results received at block 202. Continuing the above example, if the cholesterol and triglyceride tests are being held, they are combined with the HDL test for the patient received at block 202. At decision block 208, it is determined whether all results for the order containing the laboratory test result received at block 202 have been performed and received. The tests may have been performed at multiple, different instruments in the laboratory. The results may also have been performed on multiple areas of modular instruments. The results from tests performed on different instruments may be received at different times. If at decision block 208 it is determined that all results for the order for the patient have not been performed and received, at block 210 the laboratory test result is held until all other results for the order are performed and received by the system.

If at block 208 it is determined that all results for the order have been performed at block 212, the laboratory test results for the order are evaluated against predefined auto-verification rules or criteria. Automatically verifying laboratory test results determines whether the test result is within a predetermined range that is considered to be acceptable for that type of laboratory test. Information regarding the patient, such as age and sex, may also be taken into account in determining what results are considered to be acceptable for the type of laboratory test.

At block 214 if it is determined that the laboratory test results passed the predefined auto-verification rules, at block 218 the laboratory test results for the order are automatically verified and at block 220 the results are released for clinical use. If at decision block 214 it is determined that one or more of the laboratory test results for the order do not pass the predefined automatic verification rules, at block 216 all the results for the order are left in a performed status and require manual verification by a clinician or technologist. For example, if one test result of an order fails to satisfy predefined auto-verification rules individually, all of the test results for the order also fail and the results are not automatically verified. In some instances, if a result cannot be manually verified, all of the tests for the order will have to be re-performed. This process prevents some test results of an order from being automatically verified when they should not have because other test results of the order failed to satisfy pre-defined rules.

Figure 3:
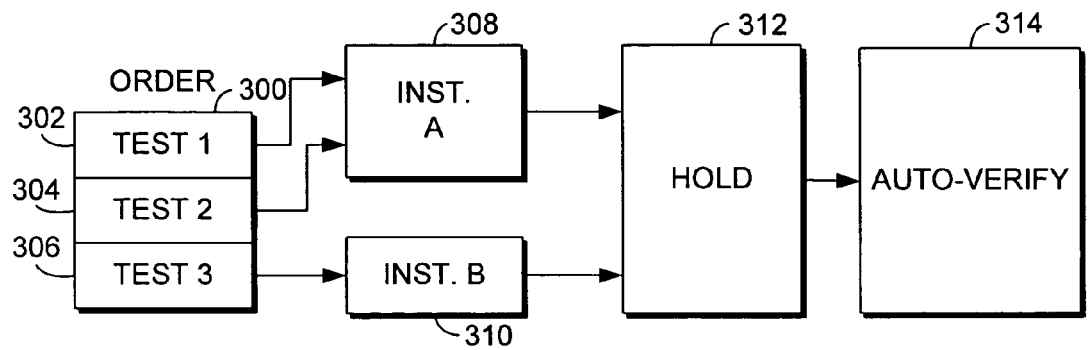
FIG. 3 is a block diagram of a computer program for automatically verifying a set of laboratory test results for an order performed by multiple instruments in accordance with an embodiment of the present invention.

By way of example, and not by limitation, the following is an example of auto-verification of multiple laboratory test results. A procedure is ordered for a fictitious patient John Smith and a sample of John Smith's blood is drawn. With reference to FIG. 3, the order 300 exemplified by a lipid profile procedure comprises three instrument-performed detailed tests, Test 1 302, Test 2 304 and Test 3 306, exemplified by a cholesterol test, a triglyceride test, and an HDL test respectively. The detailed tests are performed on two different instruments, Instrument A 308 and Instrument B 310. Instrument A 308 is exemplified by a VITROS 950 instrument and Instrument B 310 by a VITROS 250 instrument.

For example, the cholesterol and triglyceride tests are performed on a VITROS 950 instrument. The HDL test is performed on a VITROS 250 instrument. After each instrument performs the necessary test on the sample received from fictitious patient John Smith, the result is sent as an electronic message and is received at block 202 of FIG. 2. The exemplary message from the VITROS 950 instrument is "VITROS 950: cholesterol=250 mg/dl; triglycerides=150 mg/dl". At block 204 of FIG. 2, it is determined whether any related results or any other results from the order related to the message received from the VITROS 950 instrument are being held. In other words, it is determined whether there are any test results that were part of the lipid profile procedure ordered for fictitious patient John Smith. At block 204, it is determined that no other results for the lipid profile procedure for fictitious patient John Smith are being held and at block 208 it is determined whether all laboratory test results for the lipid profile have been performed. At decision block 208, it is determined that all of the laboratory test results for the lipid profile procedure have not been performed and received and there is one test result remaining to be received. The test result still needed is the result for the HDL detail test. As such, at block 210 the laboratory test result message received from the VITROS 950 instrument is placed on hold until all of the other laboratory results for the lipid profile procedure have been performed and received. The hold process is exemplified by block 312 of FIG. 3.

At block 202, another completed laboratory test result message from the VITROS 250 instrument for the HDL detail test for fictitious patient John Smith is received. The exemplary message from the VITROS 250 instrument is "VITROS 250: HDL=<4 mg/dl". At block 204 of FIG. 2, it is determined whether there are any related results to the message received being held. It is determined that another message for the lipid profile procedure for fictitious patient John Smith from the VITROS 950 instrument is being held. At block 206, the related result that is being held is combined with the result from the VITROS 250 instrument.

At block 208, it is determined that all results for the order have been performed and received as the results for the cholesterol test, triglyceride test, and the HDL test for fictitious patient John Smith have all been received from their respective instrument or medical devices. Because all of the test results for the lipid profile procedure for patient John Smith have been received, the results are evaluated against predefined auto-verification rules. It is determined at block 214 that only two of the test results satisfy the predefined auto-verification rules and are within the predefined ranges for each type of procedure. Thus, since one result has failed auto-verification, at block 218 the entire lipid profile order for patient John Smith including the three results from two different instruments are not auto-verified. The auto-verification process is exemplified by block 314 of FIG. 3.

Figure 4:
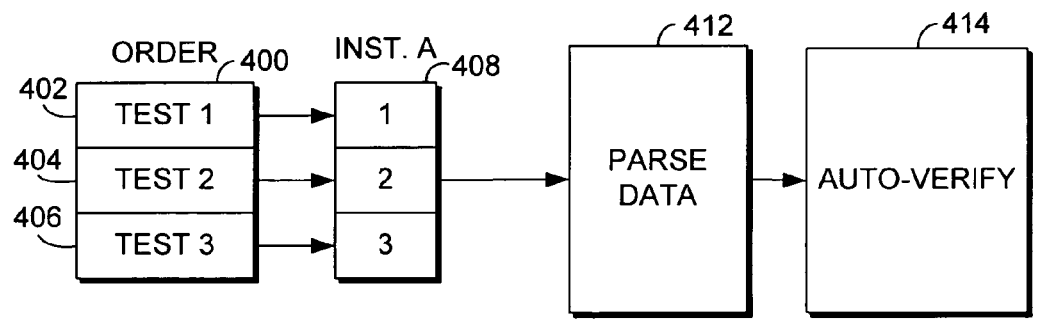
FIG. 4 is a block diagram of a computer program for automatically verifying multiple laboratory test results from a modular laboratory instrument in accordance with an embodiment of the present invention.

Referring next to FIG. 4, by way of example, and not by limitation, an order 400 for a patient comprising three tests, Test 1 402, Test 2 404 and Test 3, 406 is sent to a modular instrument 408, such as a Modular Analytics SWA (Serum Work Area) produced and sold by Roche Diagnostics. A modular laboratory instrument performs multiple laboratory tests in a different area of the instrument. For example, each of the three Tests 402, 404 and 406 of order 400 is performed in a different area of the modular instrument 408. For example, Test 1 is performed in area 1, Test 2 is performed in area 2 and Test 3 is performed in area 3 of modular instrument 408. The test results for all three of the tests are combined into one data stream received by the auto-verification system. At block 412 the results data stream from the modular instrument 408 is parsed into separate results for each individual test. At block 414, it is determined whether each of the parsed laboratory test results for the order satisfy predefined auto-verification rules. If one test result in an order fails to satisfy predefined auto-verification rules individually, the rules may require that all of the test results for the order fail and are not automatically verified.

The present invention, has been described in relation to particular embodiments, which are intended in all respects to illustrative rather than restrictive. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims.

The invention claimed is:

1. A method of receiving data from a modular laboratory instrument, wherein the modular laboratory instrument performs multiple laboratory tests, the method comprising:
   one or more computing devices executing:
      receiving data from two or more modular laboratory instruments, the data comprising laboratory test results for one or more laboratory tests for an order, wherein the order is a lipid profile comprising a cholesterol test, a triglyceride test, and an HDL test;
      parsing the data from the modular laboratory instruments into individual test results for the order;
      determining whether all of the test results for the order have been performed and received;
      if all of the test results for the order have not been performed and received, holding the test results that have been performed and received until all of the test results have been performed and received: and
      if all of the test results for the order have been performed and received, comparing each of the individual test results in the healthcare order to a predefined criteria to determine whether each of the individual test results are considered to be normal, the predefined criteria including personal information about the patient who is associated with the laboratory tests, the personal information comprising an age and a gender of the patient, wherein,
      if each of the test results is considered to be normal, automatically verifying the entire order, thereby releasing the results for clinical use, and
      if each of the test results is not considered to be normal, performing each of the healthcare test in the order again.

2. The method of claim 1, further comprising:
   receiving the data from an interfaced laboratory instrument.

3. The method of claim 2, wherein the data received is an electronic message.

4. The method of claim 1, wherein the healthcare order comprises a set of healthcare related tests.

5. A system having a computer to perform a method for suspending processing of laboratory test results in a computerized environment, the system comprising:
   the computer configured to execute:
      a receiving component for receiving a first laboratory test result for a patient, wherein the healthcare order is a lipid profile and comprises multiple tests including a cholesterol test, a triglyceride test, and an HDL test, and wherein the receiving component receives two or more of the test results for the healthcare order from different laboratory instruments;
      a determining component for determining whether all of the test results for the healthcare order have been received;
      a comparing component for comparing each of the test results for the healthcare order to a predefined criteria to determine whether each of the test results is considered to be normal, the predefined criteria including personal information about the patient who is associated with the laboratory tests, the personal information comprising an age and a gender of the patient;
      a suspending component for suspending processing of the first laboratory test result if all of the test results for the order have not been received, otherwise forwarding all the test results to a verifying component;
      the verifying component for automatically verifying the entire order if all of the test results have been received and are considered to be normal;
      if each of the test results is considered to be normal, automatically verifying the entire order, thereby releasing the results for clinical use, and
      if each of the test results is not considered to be normal, performing each of the healthcare test in the order again.

6. The system of claim 5, wherein the receiving component receives the first laboratory test result for a patient from an interfaced laboratory instrument.

7. The system of claim 5, wherein the first laboratory test result is an electronic message.

8. The system of claim 5, further comprising:
   a second receiving component for receiving a second laboratory test result for a healthcare order for a patient; and
   a second determining component for determining whether all of the test results for the healthcare order have been received, wherein if all of the results for the healthcare order have been received, a comparing component compares each to redefined criteria to determine whether each test result for the healthcare order is within an acceptable range.

* * * * *